United States Patent [19]
Chandra et al.

[11] 3,992,427
[45] Nov. 16, 1976

[54] PREPARATION OF ORGANOSILICON COMPOUNDS

[75] Inventors: Grish Chandra, Penarth; Brian John Griffiths, Coytrahen, near Bridgend; Stephen Westall, Barry, all of Wales

[73] Assignee: Dow Corning Limited, Barry, Wales

[22] Filed: Feb. 20, 1976

[21] Appl. No.: 659,806

[30] Foreign Application Priority Data

Feb. 25, 1975 United Kingdom.................. 7729/75

[52] U.S. Cl. .................... 260/448.2 E; 260/46.5 R; 260/448.8 R
[51] Int. Cl.² ......................... C07F 7/08; C07F 7/18
[58] Field of Search ................ 260/448.2 E, 46.5 R, 260/448.8 R

[56] References Cited
UNITED STATES PATENTS

| | | | |
|---|---|---|---|
| 3,198,766 | 8/1965 | Nitsche et al. .................. | 260/46.5 R |
| 3,271,362 | 9/1966 | Chalk et al. ............... | 260/448.2 E X |
| 3,470,225 | 9/1969 | Knorre et al. ................. | 260/448.2 E |
| 3,714,212 | 1/1973 | Lengnick....................... | 260/448.2 E |
| 3,864,372 | 2/1975 | Svoboda et al. .............. | 260/448.2 E |

*Primary Examiner*—Paul F. Shaver
*Attorney, Agent, or Firm*—Robert F. Fleming, Jr.

[57] ABSTRACT

Process for preparing an organosilicon product by the reaction of a silicon compound having SiH groups with an organic or organosilicon compound having aliphatic unsaturation in the molecule. The process is carried out in the presence of, as catalyst, a compound or complex of platinum or rhodium and also in the presence of a cobalt salt of a monocarboxylic acid. The cobalt salt improves the catalytic performance of the compound or complex of platinum or rhodium.

3 Claims, No Drawings

PREPARATION OF ORGANOSILICON COMPOUNDS

This invention relates to a process for the preparation of organosilicon products.

The reaction of silicon compounds having silicon-bonded hydrogen atoms with compounds having aliphatic unsaturation has long been known in the art of organosilicon chemistry. Such a reaction provides a commercially useful route to many types of organosilicon products. The reaction is utilised, for example, for the synthesis of organosilanes and organosiloxanes and also for the crosslinking of organosiloxane polymers to produce potting gels and rubbers. It is normally carried out in the presence of a catalyst, the most widely employed catalysts being the platinum metals and compounds and complexes of such metals. Of particular utility as catalysts are the platinum and rhodium compounds, for example chloroplatinic acid, rhodium trichloride and complexes formed by the combination of such compounds with unsaturated compounds such as cyclohexene, vinyl-substituted siloxanes or with organic thiol compounds. However, although such compounds and complexes are generally effective as catalysts it is often desired to improve their catalytic performance. For example, the induction period with respect to some reactions may vary from seconds to hours. Also, there are many reactions, such as in the preparation of certain types of silicone rubber products, where increased catalytic activity resulting in reduced curing (reaction) time is desired. With respect to the latter some reduction of reaction time is possible by increasing the proportion of catalyst. Platinum metals are however expensive materials and economic considerations dictate their use in the lowest possible proportions.

We have now found that the above recited drawbacks associated with the use of platinum and rhodium compounds as SiH addition catalysts can be minimised by including in the reaction mixture a cobalt salt of a monocarboxylic acid.

Accordingly this invention provides a process for the preparation of an organosilicon product which comprises reacting (A) a silicon compound having in the molecule at least one silicon-bonded hydrogen atom and (B) an organic or organosilicon compound having in the molecule aliphatic carbon atoms linked by multiple bonds in the presence of (C) a compound or complex of platinum or rhodium and (D) a cobalt salt of a monocarboxylic acid, (A) and (B) being free of silicon-bonded halogen atoms.

Also included within the scope of the invention are organosilicon products whenever obtained by said reaction.

Any silicon compound having in the molecule at least one silicon-bonded hydrogen atom can be used as reactant (A), with the proviso that the compound should be free of silicon-bonded halogen atoms. It may therefore be a monomer, a polymer or a copolymer or a mixture of any of these materials. Thus it may be a silane or polysilane, for example $HSi(OCH_3)_3$, $HSi(OC_4H_9)_3$, $HSi(CH_3)_3$, $HSi(C_2H_5)_3$, $HSiCH_3(OC_2H_5)_2$, $H_2Si(C_2H_5)_2$, $HSi(C_6H_5)_2CH_3$, and $(CH_3)_2HSiSiH(CH_3)_2$. The silicon compound (A) may also be a low molecular weight organosiloxane or a polyorganosiloxane for example a disiloxane $R_2HSiOSiHR_2$ or a cyclic siloxane $(RHSiO)_n$ in which $n$ is for example 3, 4 or 5 and R is an organic radical, an organosiloxane polymer or an organosiloxane copolymer. Specific operative organosiloxanes and polyorganosiloxanes are tetramethyldisiloxane, tetramethylcyclo-tetrasiloxane, methylhydrogen polysiloxanes and copolymers of methylhydrogensiloxane units and for example one or more of dimethylsiloxane units, trimethylsiloxane units, methyltrifluoropropylsiloxane units and phenyldimethylsiloxane units.

The nature of the silicon-bonded substituents present in the silicon compounds in addition to the silicon-bonded hydrogen atoms is not critical except that they should not be halogen. Such substituents may be for example alkoxy radicals, alkoxyalkoxy radicals, monovalent hydrocarbon radicals and monovalent halogenated hydrocarbon radicals, preferably those having from 1 to 18 carbon atoms. Examples of such radicals are methyl, ethyl, propyl, 2,4,4-trimethylpentyl, phenyl, 3,3,3-trifluoropropyl, methoxy, ethoxy, hexoxy and methoxyethoxy radicals.

Reactant (B) having aliphatic unsaturation in the molecule may be organic, for example, pentene-1, hexene-2, heptene-1, acetylene, butadiene, vinylacetylene, cyclohexene, styrene, allyl bromide, vinyl acetate or allyl alcohol, or it may be organosilicon, for example $(CH_3)_2(CH_2\!\!=\!\!CH)Si(OC_2H_5)$, $(CH_2\!\!=\!\!CH)Si(OCH_3)_3$, $(CH_2\!\!=\!\!CH)Si(C_2H_5)_3$ and organosiloxanes and polyorganosiloxanes having in the molecule vinyl, allyl or styryl radicals. Any remaining silicon-bonded substituents in the unsaturated organosilanes and siloxanes may be, for example, alkoxy and alkoxyalkoxy radicals, monovalent hydrocarbon radicals and monovalent halogenated hydrocarbon radicals, as exemplified for reactant (A). In view of their wider commercial availability and application the preferred unsaturated organosilicon compounds are those in which any remaining substituents are methyl and/or phenyl radicals.

As the catalyst (C) there may be employed in the process of this invention any of the platinum or rhodium compounds or complexes useful as catalysts in SiH addition reactions. A wide variety of such compounds and complexes are known and include for example chloroplatinic acid, platinic chloride, platinum acetylacetonate, complexes obtained by reacting platinum compounds with unsaturated compounds such as cyclohexene and vinyl-containing organosiloxanes, complexes containing platinum and sulphur, complexes containing platinum and phosphorus, $RhCl_3 \times H_2O$, diethylene rhodium (I) acetyl acetonate and complexes containing rhodium and sulphur. The catalyst (C) may be used in conventional proportions the actual amounts in any particular instance depending on the nature of the reaction. Preferably the catalyst (C) is employed in a proportion that provides from about $10^{-5}$ to $10^{-3}$ mole of elemental Pt or Rh per mole of SiH in the reaction mixture.

Component (D) may be the cobalt salt of any monocarboxylic acid and may be for example cobalt acetate, cobalt octoate, cobalt lactate, cobalt oleate and cobalt resinate. Preferred as component (D) are the cobalt naphthenates. Said naphthenates, like certain of the other cobalt carboxylates are well-known substances and are normally commercially available as paint driers. They are derived from the naphthenic acids, a petroleum by-product, and the composition of cobalt naphthenate may vary depending on the source. Such variations are however not critical to the success of this invention. The proportion of cobalt carboxylate employed in the reaction mixture is not narrowly critical. Best results appear to be achieved when the proportion of cobalt to Pt or Rh is in the range of from 0.5/1 to 5/1 by weight.

In general the reaction involving (A), (B), (C) and (D) may be carried out under reaction conditions normally employed for SiH addition. It may be performed in the presence or absence of solvents. For example when the process involves the synthesis of a specific compound it may be desirable to employ an organic solvent to assist in the reaction itself or recovery of the product. When the process involves the crosslinking of a rubber, or the formation of a potting gel, the reaction may take place in the absence of a solvent. Elevated temperatures and pressures may also be employed if desired.

The following Examples in which Me represents the methyl radical and Vi the vinyl radical illustrate the invention.

EXAMPLE 1

$(Me_3SiO)_2SiMeH$ (0.05 mole; 11.1 g.), 1-decene (0.05 mole; 7.0 g.) and cobalt naphthenate (0.064 g.) (containing 6% by weight of cobalt) were placed in a flask at room temperature under nitrogen. To the contents of the flask was then added a 10% solution in isopropanol of $H_2PtCl_6 6H_2O/(5 \times 10^{-4}$ mole; 129.5 $\mu$l) and the time taken for the reaction mixture to reach its maximum temperature was measured. No external heat was supplied to the reaction mixture.

The procedure was repeated employing the same and different weights of cobalt naphthenate, the reaction being carried out under air and under nitrogen. The times taken for the attainment of maximum temperature (termed reaction time) in each case are set out in the following table.

| Cobalt Naphthenate (g) | Reaction Time (min.) Nitrogen | Air |
|---|---|---|
| 0 | 125 | 81½ |
| 0 | 65 | — |
| 0.032 | 50 | 15.25 |
| 0.064 | 10½ | 7.25 |
| 0.064 | 15 | 7.5 |
| 0.129 | 20½ | 12.3 |
| 0.258 | 26 | — |

The data set out in the table indicates the inconsistent results obtained when no cobalt naphthenate is present, and the improvement in reaction times which results when cobalt naphthenate is added.

EXAMPLE 2

The procedure described in Example 1 was repeated employing cobalt lactate in place of the cobalt naphthenate; all of the reactions being performed in air. The times taken to attain maximum temperature were as follows:

| Cobalt Lactate (g) | Reaction Time (min.) |
|---|---|
| 0 | 48 |
| 0.0179 | 17 |
| 0.0717 | 15 |
| 0.3586 | 10 |

Similar results were obtained when the cobalt lactate was replaced by cobalt siccatol.

EXAMPLE 3

A composition was prepared by mixing the following, the parts being expressed by weight:

| | | |
|---|---|---|
| Polydimethylsiloxane end-stopped with dimethylvinylsiloxy units (viscosity 2000 cP at 25° C) | 49.5 | parts |
| Diatomaceous silica | 21.78 | parts |
| Calcium carbonate | 27.7 | parts |
| Platinum complex* | 0.99 | parts |
| Cobalt naphthenate | to give 18 ppm Co | |

*The platinum complex was a reaction product of $H_2PtCl_6 . 6H_2O$ and tetramethyldivinyldisiloxane and contained 0.645% by weight of elemental platinum.

A second composition was prepared by mixing:

| | | |
|---|---|---|
| Polydimethylsiloxane end-stopped with dimethylvinylsiloxy units (viscosity 2,000 cP at 25° C) | 89.1 | parts |
| Fume silica | 9.81 | parts |
| $Si(OSiHMe_2)_4$ | 1.0 | parts |

One part by weight of each of the above compositions was taken and the two parts mixed together for one minute. The resulting mixture hardened to a rubber in 8 minutes at 22° C.

When the procedure was repeated with the cobalt naphthenate omitted the mixture required 15 minutes at 22° C to harden to a rubber.

EXAMPLE 4

A methylvinyl cyclic siloxane $(MeViSiO)_4$ (7.6 g.) and a methylhydrogen cyclic siloxane $(MeHSiO)_4$ (6.0 g.) were placed in a flask and a 10% w/v solution (100$\mu$l) of $H_2PtCl_6.6H_2O$ in isopropyl alcohol added with stirring. The temperature of the reaction mixture increased slowly from 25° to 35° C over 10 minutes, the temperature thereafter increasing rapidly to above 200° C.

The process was then repeated, cobalt naphthenate (0.1 g.) being added to the flask with the cyclic siloxanes. Reaction occurred immediately on addition of the platinum catalyst and the temperature rose to above 200° C within 3 minutes.

That which is claimed is:

1. A process for the preparation of an organosilicon product which comprises reacting (A) a silicon compound having in the molecule at least one silicon-bonded hydrogen atom and (B) an organic or organosilicon compound having in the molecule aliphatic carbon atoms linked by multiple bonds, in the presence of (C) a compound or complex of platinum or rhodium and (D) a cobalt salt of a monocarboxylic acid, (A) and (B) being free of silicon-bonded halogen atoms.

2. A process as claimed in claim 1 wherein the cobalt salt (D) is cobalt naphthenate.

3. A process as claimed in claim 1 wherein (C) and (D) are employed in proportions such that the weight ratio of cobalt in (D) to platinum or rhodium in (C) is from 0.5/1 to 5/1.

* * * * *